United States Patent [19]
Wade et al.

[11] 3,981,881
[45] Sept. 21, 1976

[54] 2-[(4-PHENYL-TETRAHYDROPYRIDINYL)ALKYL]-1H-ISOINDOLE-1,3(2H)-DIONES

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Aug. 14, 1975

[21] Appl. No.: 604,748

[52] U.S. Cl. .................. 260/295 M; 260/294.8 C; 260/294.9; 424/263
[51] Int. Cl.² ........................................ C07D 211/70
[58] Field of Search .... 260/295 K, 295 M, 294.8 C, 260/294.9

[56] References Cited
UNITED STATES PATENTS

| 2,498,497 | 2/1950 | Kirchner et al. | 260/295 M |
| 3,481,935 | 12/1969 | Tomcufcik et al. | 260/293 |
| 3,579,524 | 5/1971 | Van Dyke, Jr. | 260/294 |

OTHER PUBLICATIONS
Chiavarelli et al., Chemical Abstracts 60:2929a, (1964).
Hideg et al., Chemical Abstracts 62:13126 d, (1965).

Primary Examiner—Norman A. Drezin
Attorney, Agent, or Firm—Lawrence S. Levinson; Merle J. Smith; Donald J. Barrack

[57] ABSTRACT
Compounds having the formula

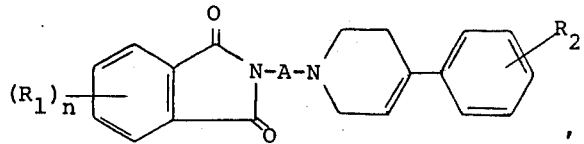

wherein A is a straight or branched chain alkylene group; $R_1$ is hydrogen, halogen, alkyl, alkoxy, alkylthio, nitro, amino, or cyano; and $R_2$ is hydrogen, halogen, alkyl, alkoxy, trifluoromethyl, nitro, amino, or cyano; and $n$ is 1 or 2, with the proviso that when $n$ is 2, $R_1$ is alkyl, alkoxy, or halogen; are useful central nervous system depressants.

10 Claims, No Drawings

2-[(4-PHENYL-TETRAHYDROPYRIDINYL)ALKYL]-1H-ISOINDOLE-1,3(2H)-DIONES

SUMMARY OF THE INVENTION

Useful central nervous system depressant activity is exhibited by compounds having the formula

I

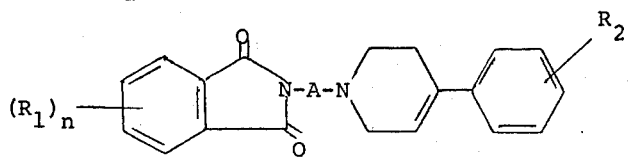

In formula I, and throughout the specification, the symbols are as defined below.

$R_1$ can be hydrogen, halogen, alkyl, alkoxy, alkylthio, nitro, amino, or cyano;

$R_2$ can be hydrogen, halogen, alkyl, alkoxy, trifluoromethyl, nitro, amino, or cyano;

A can be a straight or branched chain alkylene group having 1 to 8 carbon atoms; and n can be 1 or 2, with the proviso that when n is 2, $R_1$ is alkyl, alkoxy, or halogen.

The term "alkyl", as used throughout the specification, refers to alkyl groups having 1 to 4 carbon atoms.

The term "alkoxy", as used throughout the specification, refers to groups having the formula Y—O— wherein Y is alkyl as defined above.

The term "alkylthio", as used throughout the specification, refers to groups having the formula Y—S— wherein Y is alkyl as defined above.

The term "halogen", as used throughout the specification, refers to fluorine, chlorine, bromine, and iodine; fluorine, chlorine and bromine are the preferred halogens.

DETAILED DESCRIPTION OF THE INVENTION

The compounds of formula I, and their pharmaceutically acceptable acid addition salts, are useful in mammalian species such as rats, dogs, monkeys, and others, as central nervous system depressants, and can be used as sedatives, e.g., to promote sleep in anxious or tense subjects. Those compounds of formula I wherein A is —CH₂—CH₂— can be used as tranquilizers for the relief of anxiety and tension states in the same manner as chlordiazepoxide. For these purposes, the compounds of this invention can be incorporated in a conventional dosage form such as tablet, capsule, injectable, or the like, along with the necessary carrier material, excipient, lubricant, buffer, or the like, for oral or parenteral administration in single or divided doses of about 1 to 100 milligrams per kilogram of body weight per day, preferably about 5 to 15 milligrams per kilogram of body weight, two to four times daily.

The products of formula I, wherein A is an alkylene group having 2 to 8 carbon atoms, can be prepared using as starting materials compounds having the formulas

II

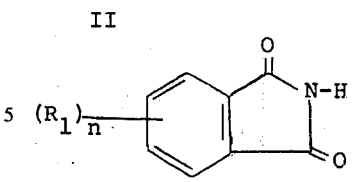

III 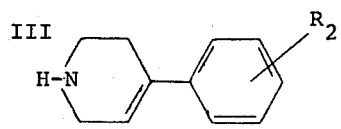 and

IV        X' - A' - X.

In formula IV, and throughout the specification, the symbol A' can be a straight or branched chain alkylene group having 2 to 8 carbon atoms and the symbols X and X' can be the same or different and can be halogen (preferably chlorine or bromine), alkylsulfonate (e.g., methanesulfonate) or arylsulfonate (e.g., toluenesulfonate).

Reaction of an isoindole-1,3-dione of formula II with a compound of IV yields an intermediate having the formula

V

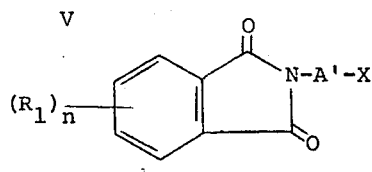

The reaction can be run in a polar organic solvent, e.g., dimethylsulfoxide or dimethylformamide, in the presence of alkali.

Reaction of an intermediate of formula V with a pyridine derivative of formula III yields the compounds of formula I wherein A is an alkylene group having 2 to 8 carbon atoms. The reaction can be run in an organic solvent, e.g., benzene, toluene, etc., preferably in the presence of an organic or inorganic base, e.g., a tertiary amine such as ethyldiisopropylamine or an alkali metal carbonate such as sodium carbonate. While reaction conditions are not critical, the reaction will most conveniently be run at the reflux temperature of the solvent.

Alternatively, the products of formula I, wherein A is an alkylene group having 2 to 8 carbon atoms, can be prepared by first reacting an isoindole-1,3-dione of formula II with an appropriate base, e.g., potassium hydroxide or thallous ethoxide. The resultant salt is reacted with a compound having the formula

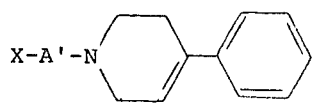

VI to yield the products of formula I wherein A is other than methylene.

In still another method for preparing the compounds of formula I wherein A is other than methylene, a phthalic anhydride derivative having the formula

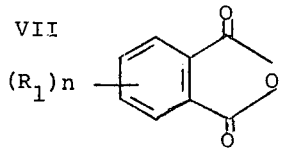

VII
$(R_1)n$ is first reacted with a compound having the formula

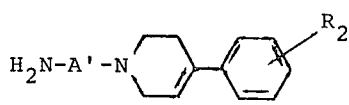

VIII to yield a compound having the formula

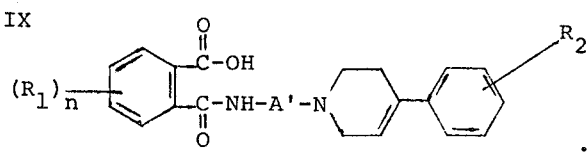

IX
$(R_1)_n$

Ring closure of a compound of formula IX using a dehydrating agent such as thionyl chloride or phosphorous oxychloride and/or heat yields the products of formula I wherein A is other than methylene.

The products of formula I wherein A is methylene are prepared using the Mannich reaction. An isoindole-1,3-dione of formula II is reacted with a pyridine derivative of formula III in the presence of formaldehyde or paraformaldehyde to yield the desired product. The reaction is run in a polar organic solvent such as dimethylformamide.

Additional procedures for preparing the compounds of this invention will be readily apparent to a person skilled in the art. For example, compounds of formula I wherein one or both of $R_1$ and $R_2$ are amino, cyano, or halogen can be prepared from the corresponding nitro compounds using well known reactions. The nitro groups can be reduced to amino groups using stannous chloride and a mineral acid such as hydrochloric acid, and the amino groups can be converted to halogen or cyano groups using the Sandmeyer reaction.

The compounds of formula I can be converted into their pharmaceutically acceptable acid addition salts using procedures well known in the art. Exemplary of the salts contemplated are the hydrohalides, especially the hydrochloride and hydrobromide which are preferred. Other inorganic salts contemplated are the nitrate, phosphate, sulfate and the like. Organic salts are also contemplated; illustrative are the tartrate, maleate, fumarate, citrate, succinate, methanesulfonate, benzenesulfonate, toluenesulfonate, and the like.

The following examples are specific embodiments of this invention.

EXAMPLE 1

2-[2-(3,6-Dihydro-4-phenyl-1(2H)-pyridinyl)ethyl]-1H-isoindole-1,3(2H)-dione, hydrochloride (1:1)

4-Phenyl-1,2,3,6-tetrahydropyridine (8.9g) is refluxed in 250ml. of toluene for 12 hours along with 12.7g of N-(2-bromoethyl)phthalimide and 6.5g of ethyldiisopropylamine. The solvent is removed in vacuo and the residue is partitioned between 10% sodium hydroxide and chloroform. The chloroform solution is dried using sodium sulfate and after removal of the drying agent, the solvent is removed in vacuo. The free base is then recrystallized from ethanol, dissolved in hot ethanol, treated with excess ethanolic hydrogen chloride solution and cooled. The precipitated salt is filtered off and dried for 4 hours at 80°C, 0.1mm. of Hg, to give 8.0g of the title compound, melting point 247°–249°C (partial decomposition).

EXAMPLE 2

2-[4-(3,6-Dihydro-4-phenyl-1(2H)-pyridinyl)butyl]-1H-isoindole-1,3(2H)-dione, hydrochloride (1:1)

4-Phenyl-1,2,3,6-tetrahydropyridine (6.35g) is refluxed for 3 days in 300ml. of toluene with 10.0g of N-(4-bromobutyl)phthalimide and about 50g of sodium carbonate. The reaction mixture is filtered while still hot, the mother liquor is washed with water and the toluene layer is separated. The solvent is removed in vacuo, and the residue is dissolved in dioxane and the salt precipitated with ethereal hydrogen chloride. Recrystallization from ethanol gives the title compound as a hemihydrate, melting point 190°–192°C.

The free base prepared from the salt has a melting point of 110°–112°C.

EXAMPLES 3–15

Following the procedure of Example 1, but substituting the compound listed in column I for N-(2-bromoethyl)phthalimide and the compound listed in column II for 4-phenyl-1,2,3,6-tetrahydropyridine, the compound listed in column III is obtained.

| Example | Column I | Column II | Column III |
|---|---|---|---|
| 3 | 4-chloro-N-(3-bromopropyl)phthalimide | 4-(4-chlorophenyl)-1,2,3,6-tetrahydropyridine | 4-chloro-2-[3-[3,6-dihydro-4-(4-chlorophenyl)-1(2H)-pyridinyl]propyl]-1H-isoindole-1,3-(2H)-dione, hydrochloride |
| 4 | 5-methylthio-N-(8-bromooctyl)phthalimide | 4-(4-bromophenyl)-1,2,3,6-tetrahydropyridine | 2-[8-[3,6-dihydro-4-(4-bromophenyl)-1(2H)-pyridinyl]octyl]-5-methylthio-1H-isoindole-1,3-(2H)-dione, hydrochloride |
| 5 | 4-ethoxy-N-(4-bromobutyl)phthalimide | 4-(2-methylphenyl)-1,2,3,6-tetrahydropyridine | 2-[4-[3,6-dihydro-4-(2-methylphenyl)-1(2H)-pyridinyl]butyl]-4-ethoxy-1H-isoindole-1,3(2H)-dione, hydrochloride |
| 6 | 5-isopropyl-N-(2-bromoethyl)phthalimide | 4-(2-methoxyphenyl)-1,2,3,6-tetrahydropyridine | 2-[2-[3,6-dihydro-4-(2-methoxyphenyl)-1(2H)-pyridinyl]ethyl]-5-isopropyl-1H-isoindole-1,3-(2H)-dione, hydrochloride |
| 7 | 4-nitro-N-(2-bromoethyl)phthalimide | 4-(4-ethylphenyl)-1,2,3,6-tetrahydropyridine | 2-[2-[3,6-dihydro-4-(4-ethylphenyl)-1(2H)-pyridinyl]ethyl]-4-nitro-1H-isoindole-1,3(2H)-dione, hydrochloride |
| 8 | 5-amino-N-(3-bromopropyl)phthalimide | 4-(4-trifluoromethylphenyl)-1,2,3,6-tetrahydropyridine | 5-amino-2-[3-[3,6-dihydro-4-(4-trifluoromethylphenyl)-1(2H)-pyridinyl]propyl]-1H-isoindole-1,3(2H)-dione, hydrochloride |
| 9 | 5-cyano-N-(4-bromobutyl)phthalimide | 4-(3-nitrophenyl)-1,2,3,6-tetrahydropyridine | 5-cyano-2-[4-[3,6-dihydro-4-(3-nitrophenyl)-1(2H)-pyridinyl]butyl]-1H-isoindole-1,3(2H)-dione, hydrochloride |
| 10 | N-(7-bromoheptyl)phthalimide | 4-(2-aminophenyl)-1,2,3,6-tetrahydropyridine | 2-[7-[3,6-dihydro-4-(2-aminophenyl)-1(2H)-pyridinyl]heptyl]-1H-isoindole-1,3(2H)-dione, hydrochloride |
| 11 | N-(2-bromoethyl)phthalimide | 4-(2-cyanophenyl)-1,2,3,6-tetrahydropyridine | 2-[2-[3,6-dihydro-4-(2-cyanophenyl)-1(2H)-pyridinyl]ethyl]-1H-isoindole-1,3(2H)-dione, hydrochloride |
| 12 | N-(3-bromo-2-methylpropyl)phthalimide | 4-pheny;-1,2,3,6-tetrahydropyridine | 2-[3-(3,6-dihydro-4-phenyl-1(2H)-pyridinyl)-2-methylpropyl]-1H-isoindole-1,3(2H)-dione, hydrochloride |
| 13 | N-(2-bromoethyl)-5,6-dimethylphthalimide | 4-phenyl-1,2,3,6-tetrahydropyridine | 2-[2-(3,6-dihydro-4-phenyl-1(2H)-pyridinyl)ethyl]-5,6-dimethyl-1H-isoindole-1,3(2H)-dione, hydrochloride |
| 14 | N-(3-bromopropyl)-4,5-dimethoxyphthalimide | 4-phenyl-1,2,3,6-tetrahydropyridine | 2-[3-(3,6-dihydro-4-phenyl-1(2H)-pyridinyl)propyl]-4,5-dimethoxy-1H-isoindole-1,3(2H)-dione, hydrochloride |
| 15 | N-(4-bromobutyl)-5,6-dichlorophthalimide | 4-phenyl-1,2,3,6-tetrahydropyridine | 5,6-dichloro-2-[4-(3,6-dihydro-4-phenyl-1(2H)-pyridinyl)butyl]-1H-isoindole-1,3(2H)-dione, hydrochloride |

EXAMPLE 16

2-[(3,6-Dihydro-4-phenyl-1(2H)-pyridinyl)methyl]-1H-isoindole-1,3(2H)-dione

4-Phenyl-1,2,3,6-tetrahydropyridine (0.025 mole) is added to 0.025 mole of phthalimide suspended in 20 ml. of dimethylformamide, followed by the addition of 2.7 ml. of 37% aqueous formaldehyde. The reaction mixture is heated at 100°C until dissolution is complete and then allowed to stand at room temperature for about 16 hours. The title compound is separated by filtration.

What is claimed is:

1. A compound having the formula

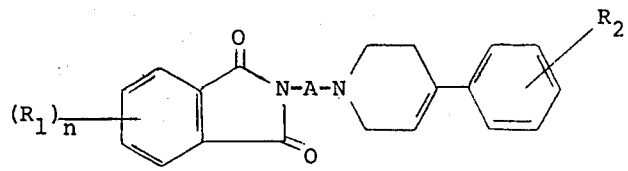

or a pharmaceutically acceptable salt thereof, wherein A is an alkylene group having 1 to 8 carbon atoms; $R_1$ is hydrogen, halogen, alkyl, alkoxy, alkylthio, nitro, amino or cyano; $R_2$ is hydrogen, halogen, alkyl, alkoxy, trifluoromethyl, nitro, amino or cyano; and *n* is 1 or 2, with the proviso that when *n* is 2, $R_1$ is alkyl, alkoxy, or halogen; wherein alkyl, alkoxy, and alkylthio are groups having 1 to 4 carbon atoms.

2. A compound in accordance with claim 1 wherein A is an alkylene group having 2 to 8 carbon atoms.

3. A compound in accordance with claim 2 wherein A is an alkylene group having 2, 3, or 4 carbon atoms.

4. A compound in accordance with claim 3 wherein A is ethylene.

5. A compound in accordance with claim 1 wherein A is methylene.

6. A compound in accordance with claim 1 wherein $R_1$ and $R_2$ are hydrogen.

7. A compound in accordance with claim 1 wherein *n* is 1.

8. The compound in accordance with claim 1 having the name 2-[2-(3,6-dihydro-4-phenyl-1(2H)-pyridinyl)ethyl]-1H-isoindole-1,3(2H)-dione, hydrochloride.

9. The compound in accordance with claim 1 having the name 2-[4-(3,6-dihydro-4-phenyl-1(2H)-pyridinyl)butyl]-1H-isoindole-1,3(2H)-dione, hydrochloride.

10. The compound in accordance with claim 1 having the name 2-[4-(3,6-dihydro-4-phenyl-1(2H)-pyridinyl)butyl]-1H-isoindole-1,3(2H)-dione.

* * * * *